US00PP32664P2

(12) United States Plant Patent
Olesen

(10) Patent No.: US PP32,664 P2
(45) Date of Patent: Dec. 22, 2020

(54) COMPACT FLORIBUNDA ROSE PLANT NAMED 'POULCAS060'

(50) Latin Name: ***Rosa* hybrid**
Varietal Denomination: Poulcas060

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,259

(22) Filed: Sep. 3, 2019

(51) Int. Cl.
*A01H 6/74* (2018.01)
*A01H 5/02* (2018.01)

(52) U.S. Cl.
USPC ..... Plt./150

(58) Field of Classification Search
USPC ..... Plt./250, 251, 150, 141
CPC ..... A01H 5/02; A01H 6/74
See application file for complete search history.

(56) References Cited

PUBLICATIONS https://www.poulsenroser.dk/en/roses/ShowProduct/53254 2020.*
PLUTO Plant Variety Database Mar. 6, 2020.p. 1.*

* cited by examiner

*Primary Examiner* — Annette H Para

(57) ABSTRACT

A new garden rose plant of the Compact Floribunda class which has abundant, red flowers and attractive foliage. This new and distinct variety has shown to be uniform and stable in the resulting generations from asexual propagation.

1 Drawing Sheet

Botanical designation: *Rosa* hybrid.
Variety denomination: 'Poulcas060'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulcas060', originated as a single seedling from the stated cross.

The new variety may be distinguished from its male pollen parent and female seed parent primarily by the following characteristics. The male pollen parent plant has ivory white flowers while the new variety has red flowers. The female seed parent plant has orange red flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulcas060' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulcas060' was selected in the spring of 2011 by the inventor as a single plant from the progeny of the aforementioned hybridization.

Asexual reproduction of 'Poulcas060' by rooted cuttings was first done by Mogens N. Olesen in the nursery in Fredensborg, Denmark in July, 2011. This initial and other subsequent asexual propagations conducted in controlled environments have demonstrated that the characteristics of 'Poulcas060' are true to type and are transmitted from one generation to the next.

DESCRIPTION OF THE DRAWING

The accompanying color illustration show as true as is reasonably possible to obtain in color photographs of this type, the typical characteristics of the buds, flowers, leaves, and stems, of 'Poulcas060'. Specifically illustrated in the drawing are open flower above and side view, a cluster of flowers on a branch, petals and sepals detached revealing reproductive flower parts, bare stem showing prickles, and leaves. Plants shown are 2 years of age.

DETAILED DESCRIPTION OF THE VARIETY

The following is a description of 'Poulcas060', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No. 22,502 are compared to 'Poulcas060' in Chart 1.

CHART 1

| | 'Poulcas060' | 'Poulcas031' |
|---|---|---|
| Petal Count | 25 petals | 40 to 50 petals |
| Flower Diameter | 72 mm | 70 to 80 mm |
| General Tonality of Flower Color | Red Group 46B with other intonations of Red-Purple Group 61A. | Purple Group N 57A |

FLOWER AND FLOWER BUD

Blooming habit: Continuous.

Flower bud:

*Size*.—Upon opening, 21 mm in length from base of receptacle to end of bud. Bud diameter is 13 mm.

*Bud form*.—Ovoid.

*Bud color*.—As sepals divide petals are Red-Purple Group 60D.

*Sepal inner surface*.—Color: Yellow-Green Group 146D. Surface: Lightly pubescent.

*Sepal outer surface*.—Color: Yellow-Green Group 144A with strong intonations of Greyed-Purple Group 183A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—18 mm long, 7 mm wide.

*Receptacle*.—Texture: Smooth. Size: 6 mm in height, 7 mm wide. Color: Yellow-Green Group 144A with light intonations of Greyed-Purple Group 183C. Shape: Funnel.

*Pedicel*.—Surface: Smooth. Length: 35 mm. Diameter: 2 mm on average. Color: Yellow-Green Group 144A with intonations of Greyed-Purple Group 183B. Strength: Strong.

*Peduncle*.—Length: 2 to 5 cm. Diameter: About 3 mm. Color: Yellow-Green Group 145A with intonations of Greyed-Purple Group 183B. Texture: Smooth.

Flower bud development: Flower buds are borne in clusters of about 5 flower buds per stem.

Flower bloom:

*Fragrance*.—Very strong perfume.

*Duration*.—The blooms have a duration on the plant of approximately 10 days. Petals fall cleanly away from plant after flowers have fully matured.

*Size*.—Flower diameter is 72 mm when open. Flower depth is 25 mm.

*Flower shape*.—Rosette double flower with many slightly overlapping petals of different sizes.

*Shape of flower, side view*.—The upper portion is flat. The lower portion is flattened concave.

Petalage: Under normal conditions, flowers have about 25 petals.

General tonality of flower: Open flowers are Red Group 46B with other intonations of Red-Purple Group 61A.

Petal color:

*Upon opening, outer petals*.—Upper surface: Red Group 46A with occasional streaks of White Group 155A. Lower surface: Red Group 54A at marginal zone. At the middle zone Red Group 45D. At the base of the petal, Yellow Group 8B.

*Upon opening, inner petals*.—Upper surface: Red Group 46A with occasional streaks of White Group 155A. Lower surface: Red Group 54A at marginal zone. At the middle zone Red Group 45D. At the base of the petal, Yellow Group 8B. Upper surface: Yellow Group 12D. Lower surface: Yellow Group 8B.

*After opening, outer petals*.—Upper surface: Red Group 46C at the middle zone, Red-Purple Group N57A at marginal zone. Lower surface: Red-Purple Group N57C at the marginal zone. At the middle zone, Red Group 43C.

*After opening, inner petals*.—Upper surface: Red Group 46C at the middle zone, Red-Purple Group N57A at marginal zone. Lower surface: Red-Purple Group N57C at the marginal zone. At the middle zone, Red Group 43C.

*Basal petal spots, after opening*.—Upper surface: Yellow Group 7C. Lower surface: Yellow Group 11B.

Petals:

*Petal reflex*.—Somewhat reflexed.

*Margin*.—Slight cleft at the margin. Strong undulations.

*Shape*.—Broad and elliptic. Apex shape: Rounded. Base shape: Acute.

*Size*.—37 mm (l)×36 mm (w).

*Texture*.—Smooth.

*Thickness*.—Average.

Petaloids:

*Size*.—7 mm (l) by 5 mm (w).

*Quantity*.—About 8.

*Shape*.—Irregular, with an acute base and rounded apices.

*Color*.—The upper surface is Red Group 46B with a petaloid basal spot of Yellow Group 8B. Under surface is Red Group 53C with a petaloid basal spot of Yellow Group 8C.

Reproductive flower parts:

*Pollen*.—None observed.

*Anthers*.—Size: 3 mm in length. Color: Yellow Group 11B. Quantity: 38 on average.

*Filaments*.—Color: Yellow Group 13C. Length: 6 mm.

*Pistils*.—Length: 4 mm. Quantity: 25 on average.

*Stigmas*.—Color: Orange-White Group 159A.

*Styles*.—Color: Green-White Group 157A.

*Location of stigmas*.—Inferior in location relative to the length of the filaments and the height of the anthers.

*Hips*.—None Observed.

PLANT

Plant growth: Upright, bushy. Plants are 45 cm in height, and 40 cm wide.

Stems:

*Color of juvenile growth*.—Yellow-Green Group 144B.

*Color of mature growth*.—Yellow-Green Group 146B with Greyed-Purple Group 183B.

*Length*.—Canes are about 20 cm from the base of the plant to the flowering portion.

*Diameter*.—About 4 mm.

*Internodes*.—On mature canes about 45 mm between nodes.

*Surface texture*.—Young wood: Smooth. Older wood: Smooth.

Long prickles:

*Incidence*.—4 prickles per 10 cm of stem.

*Size*.—Average length of prickles on mature stems is 4 mm.

*Shape*.—Upper portion is linear. Lower portion is concave.

*Color*.—Juvenile prickles: Greyed-Red Group 179B. Mature prickles: Greyed-Red Group 179B.

Plant foliage:

*Compound leaf*.—100 mm (l)×70 (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 147C.

Plant leaves and leaflets:

*Stipules*.—Size: 11 mm long, mm wide. Quantity: 2 per compound leaf. Shape: Linear, slightly broad based with outward extending apices. Margins: Finely serrated. Color: Yellow-Green Group 144A.

*Petiole*.—Length: 22 mm. Diameter: 1.5 mm. Upper surface color: Yellow-Green Group 144A with intonations of Greyed-Purple Group 183B. Lower surface color:

*Rachis*.—Length: 30 mm. Upper surface color: Yellow-Green Group 144A with intonations of Greyed-Purple Group 183B. Lower surface color: Yellow-Green Group 144A.

*Leaflet*.—Quantity: Normally 5 leaflets. Margins: Serrated. Size: Terminal leaflets are about 41 mm long, 30 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas060', substantially as illustrated and described herein, due to its abundant red flowers, disease resistance, and extended period of bloom.

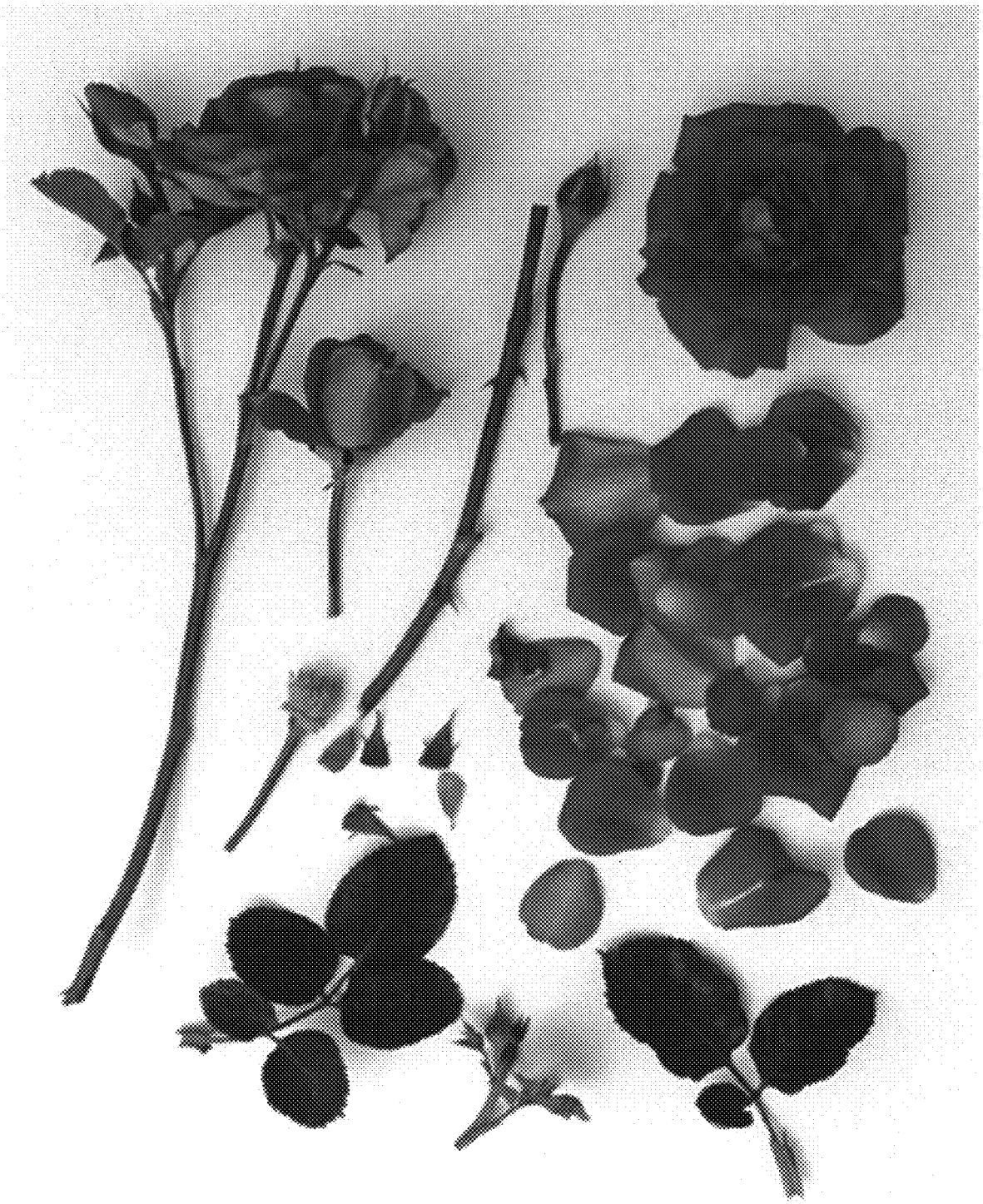

* * * * *